United States Patent
Vincent

(10) Patent No.: US 7,037,328 B2
(45) Date of Patent: May 2, 2006

(54) INJECTOR FOR AN INTRAOCULAR LENS

(75) Inventor: Patrice Vincent, Mevoisins (FR)

(73) Assignee: Laboratoire de Contactologie Appliquee-LCA, Chartres (FR)

( * ) Notice: Subject to any disclaimer, the term of this patent is extended or adjusted under 35 U.S.C. 154(b) by 0 days.

(21) Appl. No.: 10/471,888

(22) PCT Filed: Mar. 12, 2002

(86) PCT No.: PCT/FR02/00870

§ 371 (c)(1),
(2), (4) Date: Jan. 16, 2004

(87) PCT Pub. No.: WO02/074202

PCT Pub. Date: Sep. 26, 2002

(65) Prior Publication Data

US 2004/0117012 A1    Jun. 17, 2004

(30) Foreign Application Priority Data

Mar. 16, 2001 (FR) .................................. 01 03636

(51) Int. Cl.
*A61F 2/16* (2006.01)
(52) U.S. Cl. ................ 623/1.12; 623/1.11; 606/107
(58) Field of Classification Search ............... 606/107; 623/6.12

See application file for complete search history.

(56) References Cited

U.S. PATENT DOCUMENTS

| | | | | |
|---|---|---|---|---|
| 4,702,244 A * | 10/1987 | Mazzocco | .................... | 606/107 |
| 4,862,885 A * | 9/1989 | Cumming | .................... | 606/107 |
| 4,957,505 A | 9/1990 | McDonald | | |
| 5,098,439 A * | 3/1992 | Hill et al. | .................... | 606/107 |
| 5,242,450 A * | 9/1993 | McDonald | .................... | 606/107 |
| 5,304,182 A * | 4/1994 | Rheinish et al. | ............ | 606/107 |
| 5,395,378 A * | 3/1995 | McDonald | .................... | 606/107 |
| 5,584,304 A * | 12/1996 | Brady | .................... | 128/898 |
| 5,620,450 A * | 4/1997 | Eagles et al. | ................ | 606/107 |
| 5,919,197 A * | 7/1999 | McDonald | .................... | 606/107 |
| 6,497,708 B1 * | 12/2002 | Cumming | .................... | 606/107 |
| 6,685,740 B1 * | 2/2004 | Figueroa et al. | ............ | 623/6.12 |

FOREIGN PATENT DOCUMENTS

| | | |
|---|---|---|
| FR | 2 789 890 | 8/2000 |
| WO | WO 96/13229 | 5/1996 |
| WO | WO 99/21514 | 5/1999 |

* cited by examiner (Continued)

OTHER PUBLICATIONS

International Preliminary Examination Report, Jun. 16, 2003.

*Primary Examiner*—Glenn K. Dawson
(74) *Attorney, Agent, or Firm*—Holland & Hart LLP

(57) ABSTRACT

An injector for injecting an intraocular lens into an eye is provided. The injector includes an optic. The optic that includes at least one lower haptic and at least one upper haptic. The injector includes a syringe body having a main portion, a cylindrical discharge portion, and a conical portion connecting the main portion to the discharge portion. A plunger moves inside the syringe body to move the lens from the main portion to the discharge portion, and out of the discharge portion. The plunger has at least two strands that move towards each other while the plunger slides inside the conical portion. When the plunger reaches the discharge portion the plunger has a profile in contact with the lens, and the profile defining at least one space to receive the at least one upper haptic of the lens.

50 Claims, 4 Drawing Sheets

INJECTOR FOR AN INTRAOCULAR LENS

The present invention relates to an injector for injecting an intraocular lens, and more particularly to such an injector that includes a multi-strand plunger.

In known manner, an intraocular lens serves to replace the lens of a patient undergoing a cataract operation. The haptic of the intraocular lens is the portion that is situated outside the "optic" or lens proper and that serves to hold the intraocular lens in position inside the eye of the patient. Usually, the lower haptic is inserted first since the incision is usually situated beside the forehead, with the surgeon being placed behind the head of the patient in the supine position during the operation. The upper haptic, which is placed last, remains the closer to the incision.

The concept of the injector appeared with the concept of intraocular lenses being made of a flexible, mechanically deformable material. This development allows small incisions to be used in cataract surgery, such incisions often being limited to about 3 millimeters (mm). The tip of the injector must be capable of passing through the incision without it being necessary to enlarge said incision.

Numerous injector models exist that use single-strand plungers for injecting intraocular lenses. In most cases, the intraocular lens is folded by an accessory device such as a cartridge with flaps, a slide, or an abutment rib, so that the function of the plunger is reduced to effecting a final thrust through the tip.

The cylindrical tip of the injector is of mean diameter (1.5 mm to 3 mm) significantly smaller than the diameter of the optic (5 mm to 7 mm) of the intraocular lens. The idea of causing the lens to pass through a cross-section that is gradually decreasing, i.e. that is of substantially conical appearance, has already been disclosed in prior patents, and in particular in Document WO 00/49974. That document discloses a multi-strand plunger in which the strands gradually come together until finally they fill the entire cross-section of the injector. That implies a risk of the lens becoming jammed between the strands of said multi-strand plunger.

An object of the present invention is to provide an intraocular lens injector that does not suffer from the above-mentioned drawbacks.

A particular object of the present invention is to provide such an injector that is simple and inexpensive to manufacture and to assemble.

In an advantageous embodiment of the present invention, provision is made for the injector to push the intraocular lens on either side by acting towards two diametrically opposite points of its optic. This provision results in preserving the angular positioning of the lens while also limiting friction. The side strands which are continuously in contact with the inside wall of the syringe prevent the lens from adhering to it. The difficulty to be overcome arises from the lens rubbing against the wall, which can destabilize it. Thus, if the lens starts to tilt, there is then a risk it might be jammed between the plunger and the wall. The object of the invention, in an advantageous embodiment thereof that associates at least two side strands pushing the intraocular lens while guiding it, is to mitigate that drawback.

In addition, while they are passing through the conical portion of the syringe, the side strands move towards each other and contribute to folding the lens, by driving it towards the axis of the system. The haptic is then simultaneously clamped via its bottom edges (action of the static cone) and via its top edges (action of the side strands).

The thrust from the side strands may be exerted either directly on the haptic, or via the upper haptic which can then be deformed. During folding, the upper haptic may be held laterally or driven towards the axis. The shape of the end of each of the side strands may thus be adapted depending on the design of the lens and inclined to various extents relative to the wall of the syringe.

At the end of folding, and in order to avoid the upper haptic being nipped between the strands and possibly the wall, spaces are provided at the ends of the strands, either in the centers or on respective sides.

Naturally, the invention is compatible with the surgeon optionally using a viscoelastic solution having lubricating properties in order to improve the process.

Since the present invention relates only to the system for pushing and folding the intraocular lens, no reference is made to the way in which said lens is loaded into the syringe body, nor to the fact that the device may include elements that are re-usable or else are for single use only. In the following embodiments, the intraocular lens ready for injection is considered to have been put in place in the system, without having undergone any deformation.

The present invention thus provides an injector for injecting an intraocular lens made up of an optic, of at least one lower haptic, and of at least one upper haptic, said injector comprising a syringe body having a preferably cylindrical main portion, a preferably cylindrical discharge portion that is preferably of smaller cross-section than the cross-section of the main portion, and a conical portion connecting said main portion to said discharge portion, a plunger being adapted to move inside said syringe body so as move said lens from the main portion to the discharge portion, and then to discharge said lens out of said discharge portion, said plunger being provided with at least two strands that can move towards each other while the plunger is sliding inside said conical portion, said injector being characterized in that, when said plunger reaches the discharge portion said plunger has a profile at its end in contact with the lens, said profile defining at least one space adapted to receive said at least one upper haptic of said lens.

Advantageously, upstream from said space, said plunger fills substantially the entire cross section of said discharge portion.

In a first embodiment, said space is central and is defined between said at least two strands of the plunger.

In a first variant, said plunger is made up of two side strands, each of which is provided with a recess on its end that is contact with the lens, the recesses being provided in those sides of the side strands that face each other, so that, when said two strands are urged together inside said discharge portion, said recesses define a central space.

In a second variant, said plunger is made up of two same-length side strands and of a shorter central strand, so that, when said side strands are urged against said central strand inside said discharge portion, said shorter central portion defines a central space between the ends of said side strands.

In another embodiment, said plunger is made up of two same-length side strands and of a longer central strand, so that, when said side strands are urged against said central strand inside said discharge portion, said longer central strand defines a side space around the longer end of said central strand.

Advantageously, said strands of the plunger are adapted to push the lens into the syringe body, the lens sliding against the walls of said syringe body and being deformed by said conical portion.

In a third embodiment, said plunger is made up of two side strands and of a central strand adapted to move relative to said side strands between a deforming position and a discharging position.

Advantageously, said lens is disposed between said side strands which form a pair of tweezers, so that said lens does not slide against the walls of said syringe body while said lens is being deformed, said deformation being implemented by said side strands which move towards each other while the plunger is sliding inside said conical portion of the syringe body.

Advantageously, said central strand moves with said side strands while said lens is being deformed, until an abutment stops said side strands, said central strand then being released from said side strands so as to discharge said deformed lens.

Advantageously, said abutment is formed where the conical portion meets the discharge portion of the syringe body.

Advantageously, said central strand has a profile defining a central or side space for receiving said at least one upper haptic of said lens.

Advantageously, said central strand is connected to said side strands via a mechanical link mechanism which automatically releases said central strand from said side strands when said side strands reach said abutment.

Advantageously, at the end of discharge of the lens, said end profile of the plunger, which profile defines said space, is disposed outside the syringe body, in particular outside said discharge portion.

Advantageously, said main portion of the syringe body is adapted to containing the lens in the non-deformed state.

Advantageously, said main portion of the syringe body is oblate in cross-section.

Other characteristics and advantages of the present invention appear more clearly from the following detailed description of four embodiments of the present invention given with reference to the accompanying drawings which are given by way of non-limiting example, and in which.

Figures 1, 2, 3:
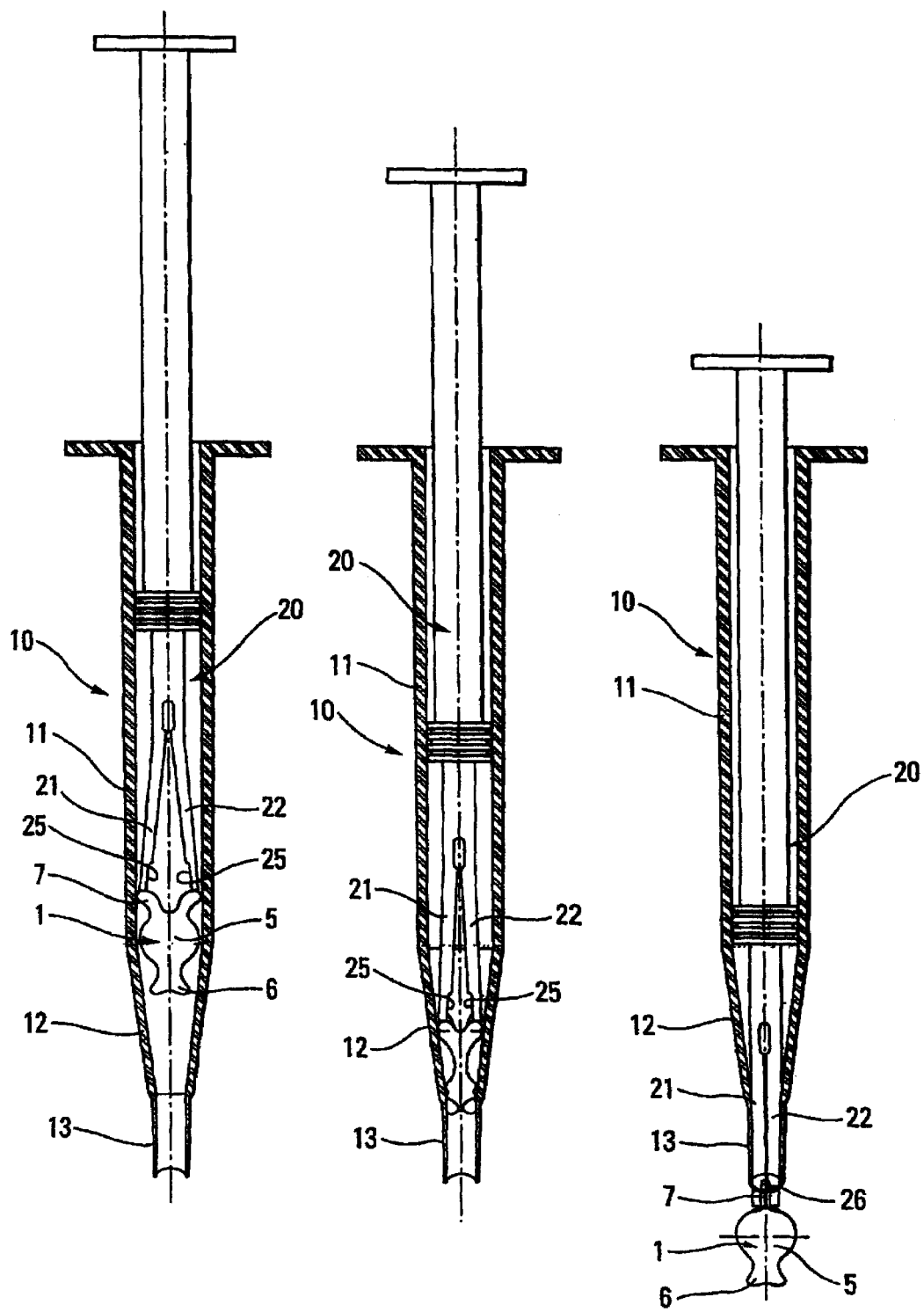
FIGS. 1 to 3 are diagrammatic section views of a first embodiment of the present invention, respectively at the start of, during, and at the end of dispensing of the intraocular lens.

FIGS. 1 to 3 show a first embodiment of the present invention. In the first embodiment, the syringe includes a body 10 made up of a cylindrical main portion 11, of a cylindrical discharge portion of cross-sectional area smaller than the cross-sectional area of the main portion 11, and of a conical portion 12 which connects said main portion 11 to said discharge portion 13. The main portion 11 is adapted to contain the lens 1 in the non-deformed state, as shown in FIG. 1. Preferably, the main portion 11 is oblate in cross-section, and it is advantageously provided with a substantially flat bottom as is described in Document WO 00/49974 which is mentioned herein by way of reference concerning the shape of the syringe body 10.

The plunger 20 is provided with two strands which can move towards each other flexibly while the plunger is sliding inside the conical portion 12. The intraocular lens 1 includes an asymmetric biconvex optic 5 which determines the direction in which it folds whenever it is compressed along its diameter. The lens includes a lower haptic 6 which is the haptic that is disposed downstream in the direction in which the lens moves inside the syringe body 10, and two symmetrical upper haptics 7 which co-operate with respective ones of said two strands of said plunger 20.

Initially, as shown in FIG. 1, the lens is disposed such that each of the two strands of the plunger 21, 22 faces a respective upper haptic 7. The optic 5 is merely guided when the plunger is actuated, and the lower haptic 6 which is narrow is engaged without contact into the conical portion 12 of the syringe 10.

When pressure is exerted on the plunger 20, the lens 1 is firstly moved in translation without being deformed until the optic comes into contact with the conical portion 12 across a diameter. When pressure continues to be exerted on the plunger 20, the upper haptics 7 deform first, as shown diagrammatically in FIG. 2, until they transmit the thrust to the edge of the optic 5 and cause it to start folding. In the intermediate position, shown in FIG. 2, the upper haptics 7 remain deformed in concertina-like manner in contact with the ends of the strands 21, 22. The optic 5 that is being folded is almost rolled up while in contact with the wall of the conical portion 12. The lower haptic 6 has started to fold by following the movement of the optic 5.

After being folded, the lens 1 is pushed into the discharge portion 13.

In the invention, the two strands 21, 22 of the plunger 20 are provided with recesses 25 at their ends in contact with the lens 1 and in particular in their facing sides, the recesses defining a profile at the end of the plunger 20. The profile is formed in a manner such that when said plunger 20 reaches the discharge portion 13 of the syringe 10, it defines a space 26 adapted to receiving the upper haptic 7 of the lens, in order to prevent said lens from being jammed between said strands of said plunger while it is being dispensed.

Once pushed into the eye, as shown in FIG. 3, the optic 5 becomes deployed again inside the eye of the patient, and the upper haptics 7 are pressed against each other in the space 26 provided for this purpose. Advantageously, as shown in FIG. 3, the strands 21, 22 of the plunger 20 fill substantially the entire cross-section of the discharge portion 13, upstream from said space 26. More particularly, at the end of discharging the lens 1, said end of the plunger 20 that incorporates the profile 25 defining the space 26 is disposed outside the syringe body 10, and in particular outside the discharge portion 13, so that the entire volume of the discharge portion 13 is filled by the plunger 20.

Advantageously, if the upper haptics 7, which are compressed to a small extent only, are not released spontaneously, it is possible to release them finally by retracting the plunger 20 to a small extent, and the intraocular lens 1 then takes up its initial shape inside the eye of the patient.

Figure 4:
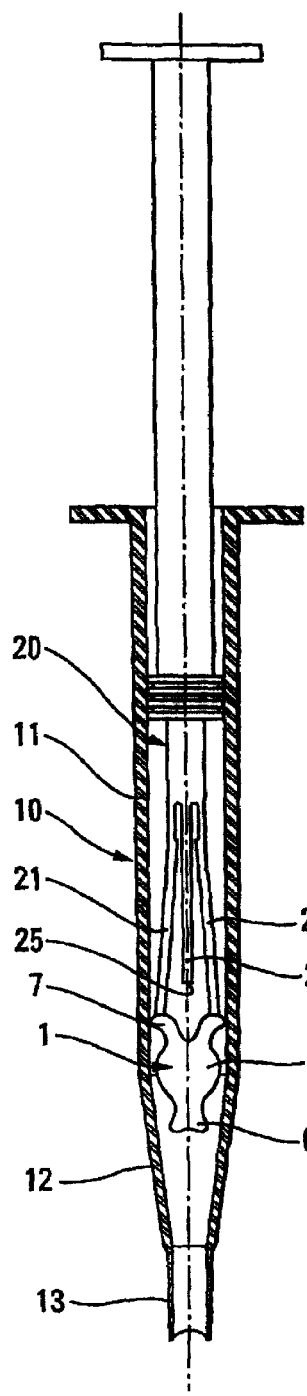
FIGS. 4 to 6 are views similar to FIGS. 1 to 3, showing a second embodiment of the present invention.
Figure 5:
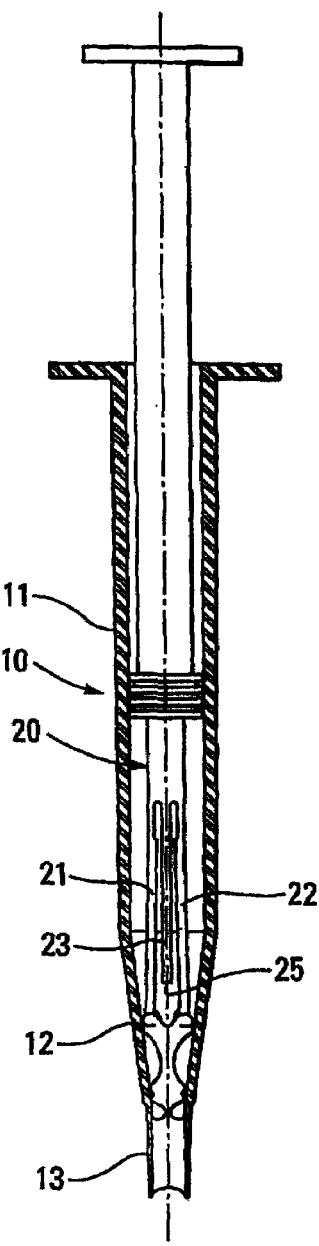
Figure 6:
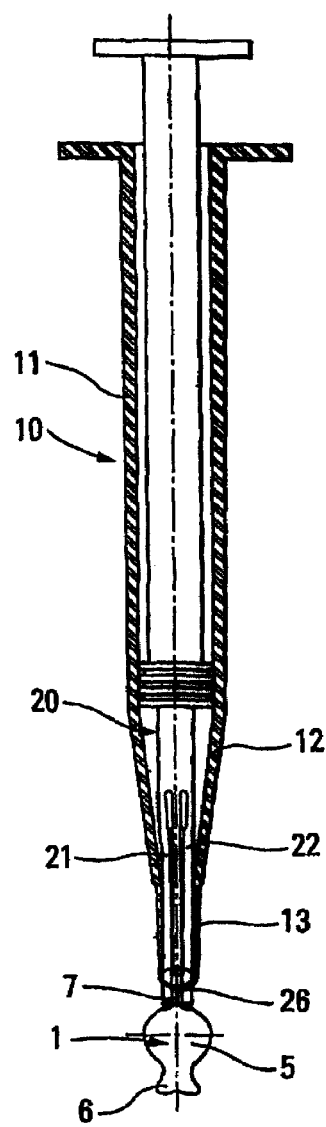

FIGS. 4 to 6 show a second embodiment of the present invention. In the second embodiment, the multi-strand plunger is made up of two side strands 21, 22 that are of the same length, and of a central strand 23 that is shorter than the two side strands 21, 22. The central strand 23 acts as a spacer which, since it is shorter in length, defines a central space 26 for receiving the upper haptic 7 of the lens 1, at the end of pushing. This device operates identically to the device described above with reference to FIGS. 1 to 3.

Figure 7:
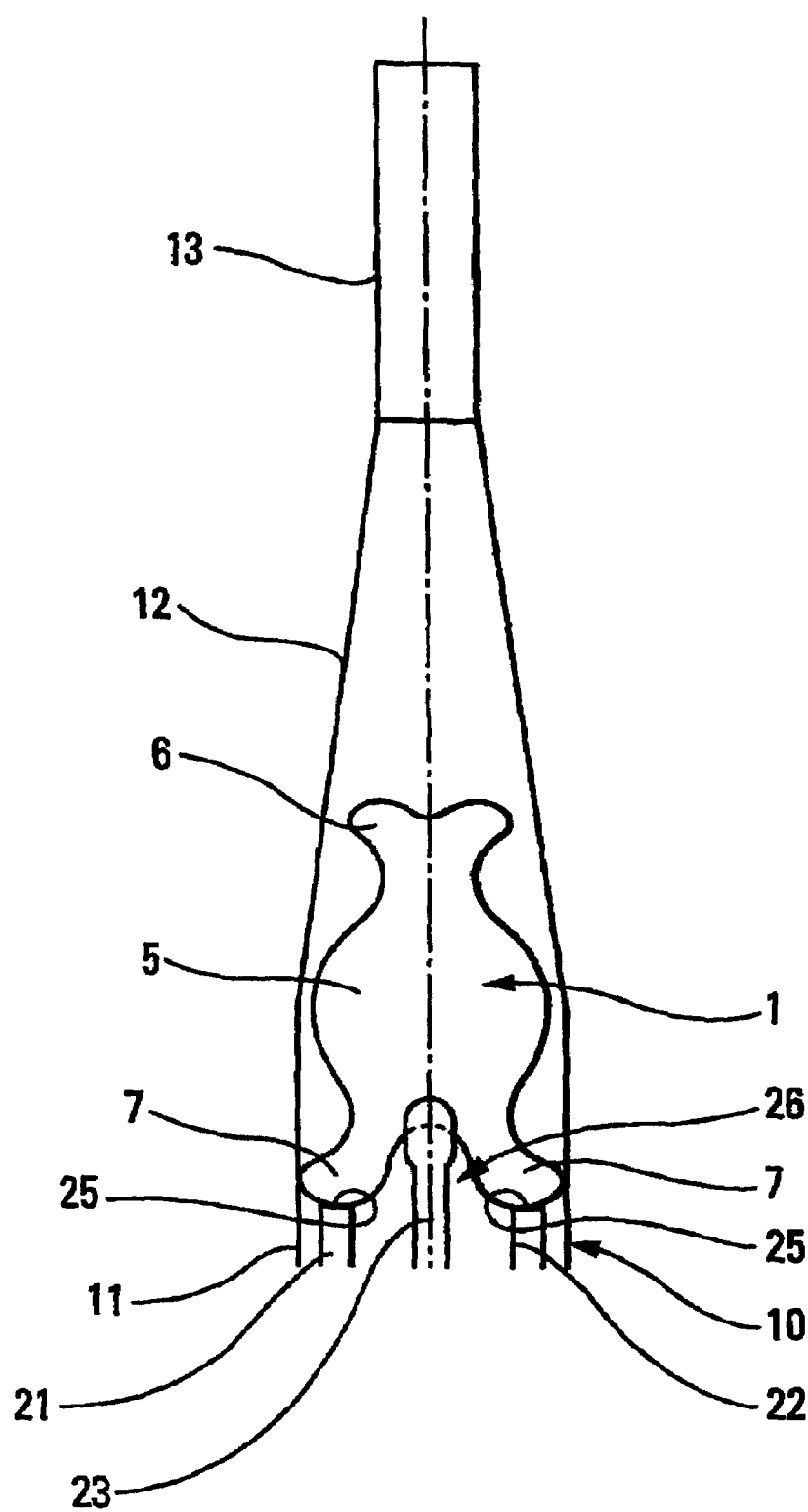
FIG. 7 is a diagrammatic section view of a third embodiment of the present invention, before the intraocular lens is dispensed.

FIG. 7 shows a third embodiment of the present invention. In the third embodiment, the plunger 20 is also made up of two same-length side strands 21, 22, as well as of a central strand 23 that is longer than the two side strands 21, 22. Said longer central strand 23 is adapted to be placed between the two upper haptics 7 of the lens, and said central strand 23 thus defines a side space 26 adapted to receive said upper haptics 7 of the lens 1. Advantageously, said central strand 23 has a wider rounded portion at its end in order to improve its contact with said lens, for the purpose of discharging it.

In all three of the embodiments described above, the plunger 20 acts to push the lens, and it is the wall or the walls of the syringe body 10 that act with said lens to deform it. More precisely, said lens 1 slides inside the syringe body 10, and in particular inside the conical portion 12 by being pushed by the strands 21, 22, and optionally 23 of the plunger, folding being obtained by the conjunction of said axial thrust from the plunger 20 and of radial drive exerted by the conical portion 12 of the syringe body 10.

Figure 8:
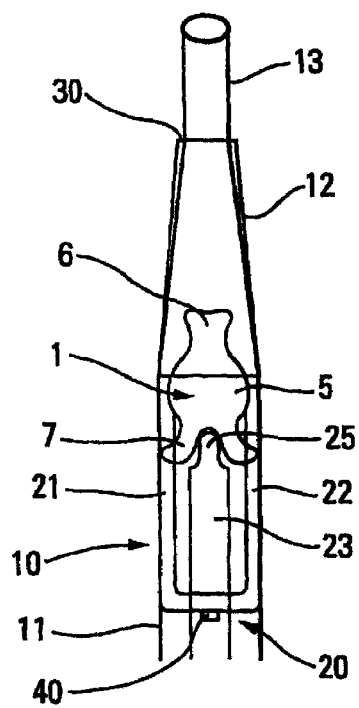
FIGS. 8 to 10 are diagrammatic section views of a fourth embodiment of the invention, respectively before, during, and at the end of dispensing of said intraocular lens.
Figure 9:
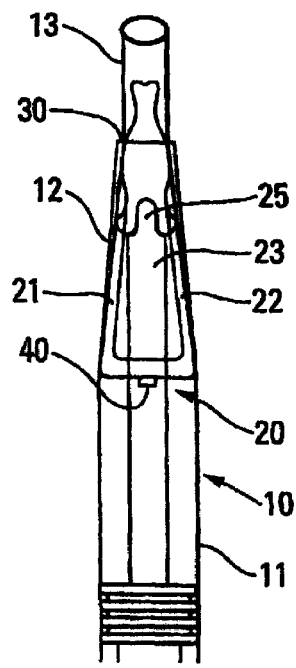
Figure 10:
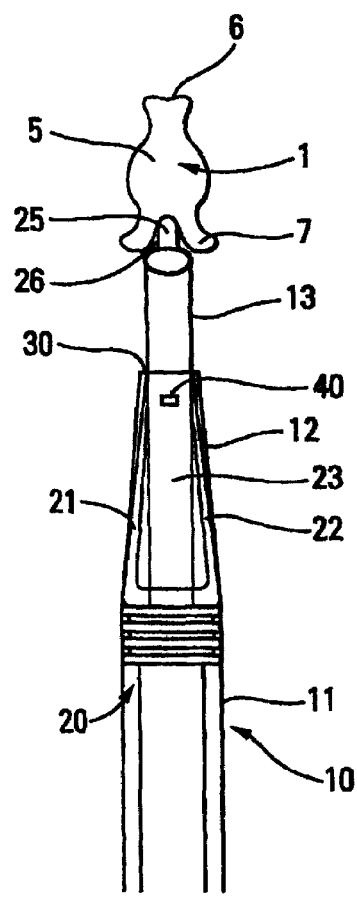

A fourth embodiment of the invention is described below with reference to FIGS. 8 to 10. In this fourth embodiment, the lens 1 does not touch the walls of the syringe body 10 until said lens 1 reaches the discharge portion 13 of said syringe body. The advantage of this embodiment is that said lens is not subjected to any axial friction against the walls of the syringe body 10 while it is folding and while it is moving towards the discharge portion 13. To this end, the plunger 20 is made up of two side strands 21, 22 which are advantageously of the same length, and which form a sort of pair of tweezers, and of a central strand 23 which is adapted to move relative to said side strands 21, 22, in particular between a deforming position and a discharging position. In this embodiment, the two side strands 21, 22 are advantageously provided with notches in order to hold the intraocular lens 1. This configuration eliminates any direct contact between the optic 5 of the lens 1 and the inside wall of the syringe body 10, so long as folding has not taken place. The friction caused by the lens 1 being moved in translation in the preceding embodiments is thus transferred between the side strands 21, 22 and the inside wall of the syringe 10, in particular in its conical portion 12. From the point of view of the intraocular lens 1, the force to which it is subjected during folding is substantially radial, while the strands 21 and 22 are moving towards each other as they are going through the conical portion 12, i.e. it is as if the lens 1 were clamped between the two jaws of a conventional pair of folding tweezers.

In this fourth embodiment, the plunger includes a central strand 23 which is secured to said side strands 21, 22 until the lens 1 is folded, i.e. until the lens reaches the discharge portion 13. Whereupon, the central strand 23 can be released from said side strands 21, 22 in order to discharge said lens through said discharge portion 13. More particularly, an abutment 30 is provided, advantageously where the conical portion 12 meets the discharge portion 13, said abutment 30 preventing said side strands 21, 22 from moving, thereby causing the central strand 23 to be released, which strand is adapted to discharge said lens 1. Thus, during the final discharge stage, the side strands 21, 22 which cannot penetrate into the injection tip 13 are held in abutment. Simultaneously, the central strand 23, which, for example, may be formed by a single central strand or by a set of central strands, continues its stroke to propel the intraocular lens through the tip or discharge portion 13. The device thus includes a system making it possible to secure the tweezer-forming side strands 21, 22 to the central strand 23 and to release them therefrom, the central strand discharging the lens 1 at the end of pushing.

Naturally, various technical solutions may be devised for achieving this, such as, for example, double coaxial plungers, an internal screw moving the central strand only, when said plunger reaches said discharge portion 13, or a connection between the side strands 21, 22 and the central strand 23 with a breakable element or hard spot that secures the elements together only until a certain thrust force is reached. It is this embodiment that is shown in the figures which show a projection 40 provided on the central strand 23 which secures said central strand to said side strands 21, 22 until said side strands come into abutment against the abutment 30 where the conical portion 12 meets the discharge portion 13. When said side strands 21, 22 come into abutment against said abutment 30, any continued thrust on the plunger 20 increases the pressure exerted on the central strand 23, which causes the portion that co-operates with the projection 40 to deform so that said central strand 23 can be released from said side strands 21, 22 in order to discharge said lens.

In the invention, in the fourth embodiment, the central strand 23 has one end 25 that defines a space 26 adapted to receive the upper haptic(s) 7 of the lens 1. As shown in the drawings, in this embodiment said profile 25 is formed by a smaller-diameter tip which comes into place between the two upper haptics 7. Naturally, it is possible to devise a different profile, e.g. a profile 25 defining a central space which is particularly well suited for receiving a lens having a single upper haptic 7.

This fourth embodiment offers the following advantages:
at the end of its movement in translation in the cylindrical portion 11 of the syringe body 10, the lens 1 is merely held in the tweezers formed by the side strands 21, 22, without being deformed;
after passing through the conical portion 12, the side strands 21, 22 are completely closed and the intraocular lens 1 is folded and engaged along the axis of the discharge portion 13 forming the tip of the syringe; the two side strands 21, 22 have come into abutment against the abutment 30, advantageously implemented in the form of two ramps serving to guide them along conical portion; the two small projections 40 acting to form a hard spot have not yet passed beyond the spacer that interconnects the two side strands 21, 22 and that secures them to said central strand 23; and
at the end of pushing, the lens 1 has been discharged and is deployed again, and the end of the central strand 23 (which is a single strand in the example shown and which defines two side spaces 26 on either side of its tip 25) has come completely out of the orifice in the discharge portion 13.

The present invention is described above with reference to four advantageous embodiments of said invention, but clearly it is not limited to these embodiments. In particular, the haptics may be of any shape, and they are not necessarily made in one piece with the optic 5 of the lens. However, a narrow lower haptic 6 advantageously co-operates with the conical shape of the conical portion 12 of the syringe. Similarly, the shape of the upper haptics 7 is particularly well suited to transmitting the thrust by said multi-strand plunger, in particular via said side strands of said plunger. In addition, lenses including haptics having separate loops, or one-piece lenses having different shapes, e.g. C-shaped loops, shuttles, haptics having four abutment points, or the like are also covered by the present invention.

Other modifications may be made by the person skilled in the art without going beyond the ambit of the present invention, as defined by the accompanying claims.

The invention claimed is:

1. An assembly comprising an injector and an intraocular lens, said intraocular lens (1) being made up of an optic (5), of at least one lower haptic (6), and of at least one upper haptic (7), said injector comprising a syringe body (10) having a cylindrical main portion (11), a cylindrical discharge portion (13) that is of smaller cross-section than the cross-section of the main portion (11), and a conical portion (12) connecting said main portion (11) to said discharge portion (13), a plunger (20) being adapted to move inside said syringe body (10) so as move said lens (1) from the main portion (11) to the discharge portion (13), and then to discharge said lens (1) out of said discharge portion (13), said plunger (20) being provided with at least two strands (21, 22) that can move towards each other while the plunger (20) is sliding inside said conical portion (12), said assembly being characterized in that, when said plunger (20) reaches the discharge portion (13) said plunger has a profile (25) at its end in contact with the lens (1), said profile defining at least one space (26) adapted to receive said at least one upper haptic (7) of said lens (1), and said plunger (20) fills substantially the entire cross section of said discharge portion (13) upstream from said space (26).

2. An assembly according to claim 1, in which said space (26) is central and is defined between said at least two strands (21, 22) of the plunger (20).

3. An assembly according to claim 2, in which said plunger (20) is made up of two side strands (21, 22), each of which is provided with a recess (25) on its end that is contact with the lens (1), the recesses being provided in those sides of the side strands that face each other, so that, when said two strands (21, 22) are urged together inside said discharge portion (13), said recesses (25) define a central space (26).

4. An assembly according to claim 2, in which said plunger (20) is made up of two same-length side strands (21, 22) and of a shorter central strand (23), so that, when said side strands (21, 22) are urged against said central strand (23) inside said discharge portion (13), said shorter central portion (23) defines a central space (26) between the ends of said side strands (21, 22).

5. An assembly according to claim 2, in which said strands (21, 22, 23) of the plunger (20) are adapted to push the lens (1) into the syringe body (10), the lens (1) sliding against the walls (11, 12, 13) of said syringe body (10) and being deformed by said conical portion (12).

6. An assembly according to claim 2, in which, at the end of discharge of the lens (1), said end profile (25) of the plunger (20), which profile defines said space (26), is disposed outside said discharge portion (13).

7. An assembly according to claim 2, in which said main portion (11) of the syringe body (10) is adapted to containing the lens (1) in the non-deformed state.

8. An assembly according to claims 1, in which said plunger (20) is made up of two side strands (21, 22), each of which is provided with a recess (25) on its end that is in contact with the lens (1), the recesses being provided in those sides of the side strands that face each other, so that, when said two strands (21, 22) are urged together inside said discharge portion (13), said recesses (25) define a central space (26).

9. An assembly according to claim 8, in which said strands (21, 22, 23) of the plunger (20) are adapted to push the lens (1) into the syringe body (10), the lens (1) sliding against the walls (11, 12, 13) of said syringe body (10) and being deformed by said conical portion (12).

10. An assembly according to claim 8, in which, at the end of discharge of the lens (1), said end profile (25) of the plunger (20), which profile defines said space (26), is disposed outside said discharge portion (13).

11. An assembly according to claim 8, in which said main portion (11) of the syringe body (10) is adapted to containing the lens (1) in the non-deformed state.

12. An assembly according to claim 1, in which said plunger (20) is made up of two same-length side strands (21, 22) and of a shorter central strand (23), so that, when said side strands (21, 22) are urged against said central strand (23) inside said discharge portion (13), said shorter central portion (23) defines a central space (26) between the ends of said side strands (21, 22).

13. An assembly according to claim 12, in which said strands (21, 22, 23) of the plunger (20) are adapted to push the lens (1) into the syringe body (10), the lens (1) sliding against the walls (11, 12, 13) of said syringe body (10) and being deformed by said conical portion (12).

14. An assembly according to claim 12, in which, at the end of discharge of the lens (1), said end profile (25) of the plunger (20), which profile defines said space (26), is disposed outside said discharge portion (13).

15. An assembly according to claim 12, in which said main portion (11) of the syringe body (10) is adapted to containing the lens (1) in the non-deformed state.

16. An assembly according to claim 1, in which said plunger (20) is made up of two same-length side strands (21, 22) and of a longer central strand (23), so that, when said side strands (21, 22) are urged against said central strand (23) inside said discharge portion (13), said longer central strand (23) defines a side space (26) around the longer end (25) of said central strand (23).

17. An assembly according to claim 16, in which said strands (21, 22, 23) of the plunger (20) are adapted to push the lens (1) into the syringe body (10), the lens (1) sliding against the walls (11, 12, 13) of said syringe body (10) and being deformed by said conical portion (12).

18. An assembly according to claim 16, in which, at the end of discharge of the lens (1), said end profile (25) of the plunger (20), which profile defines said space (26), is disposed outside said discharge portion (13).

19. An assembly according to claim 16, in which said main portion (11) of the syringe body (10) is adapted to containing the lens (1) in the non-deformed state.

20. An assembly according to claim 1, in which said strands (21, 22, 23) of the plunger (20) are adapted to push the lens (1) into the syringe body (10), the lens (1) sliding against the walls (11, 12, 13) of said syringe body (10) and being deformed by said conical portion (12).

21. An assembly according to claim 20, in which, at the end of discharge of the lens (1), said end profile (25) of the plunger (20), which profile defines said space (26), is disposed outside said discharge portion (13).

22. An assembly according to claim 20, in which said main portion (11) of the syringe body (10) is adapted to containing the lens (1) in the non-deformed state.

23. An assembly according to claim 1, in which said plunger is made up of two side strands (21, 22) and of a central strand (23) adapted to move relative to said side strands (21, 22) between a deforming position and a discharging position.

24. An assembly according to claim 23, in which said lens (1) is disposed between said side strands (21, 22) which form a pair of tweezers, so that said lens does not slide against the walls (11, 12, 13) of said syringe body (10) while said lens is being deformed, said deformation being implemented by said side strands (21, 22) which move towards each other while the plunger (20) is sliding inside said conical portion (12) of the syringe body (10).

25. An assembly according to claim 24, in which said central strand (23) moves with said side strands (21, 22) while said lens (1) is being deformed, until an abutment (30) stops said side strands (21, 22), said central strand (23) then being released from said side strands (21, 22) sp as to discharge said deformed lens (1).

26. An assembly according to claim 24, in which, at its end in contact with the lens (1), said central strand (23) has a profile (25) defining a central or side space (26) for receiving said at least one upper haptic of said lens (1).

27. An assembly according to claim 24, in which, at the end of discharge of the lens (1), said end profile (25) of the plunger (20), which profile defines said space (26), is disposed outside said discharge portion (13).

28. An assembly according to claim 24, in which said main portion (11) of the syringe body (10) is adapted to containing the lens (1) in the non-deformed state.

29. An assembly according to claim 23, in which said central strand (23) moves with said side strands (21, 22) while said lens (1) is being deformed, until an abutment (30) stops said side strands (21, 22), said central strand (23) then being released from said side strands (21, 22) so as to discharge said deformed lens (1).

30. An assembly according to claim 29, in which said abutment (30) is formed where the conical portion (12) meets the discharge portion (13) of the syringe body (10).

31. An assembly according to claim 30, in which, at its end in contact with the lens (1), said central strand (23) has a profile (25) defining a central or side space (26) for receiving said at least one upper haptic of said lens (1).

32. An assembly according to claim 30, in which said central strand (23) is connected to said side strands (21, 22) via a mechanical link mechanism (40) which automatically releases said central strand (23) from said side strands (21, 22) when said side strands reach said abutment (30).

33. An assembly according to claim 30, in which, at the end of discharge of the lens (1), said end profile (25) of the plunger (20), which profile defines said space (26), is disposed outside said discharge portion (13).

34. An assembly according to claim 30, in which said main portion (11) of the syringe body (10) is adapted to containing the lens (1) in the non-deformed state.

35. An assembly according to claim 29, in which said central strand (23) is connected to said side strands (21, 22) via a mechanical link mechanism (40) which automatically releases said central strand (23) from said side strands (21, 22) when said side strands reach said abutment (30).

36. An assembly according to claim 35, in which, at the end of discharge of the lens (1), said end profile (25) of the plunger (20), which profile defines said space (26), is disposed outside said discharge portion (13).

37. An assembly according to claim 13, in which said main portion (11) of the syringe body (10) is adapted to containing the lens (1) in the non-deformed state.

38. An assembly according to claim 29, in which, at its end in contact with the lens (1), said central strand (23) has a profile (25) defining a central or side space (26) for receiving said at least one upper haptic of said lens (1).

39. An assembly according to claim 29, in which, at the end of discharge of the lens (1), said end profile (25) of the plunger (20), which profile defines said space (26), is disposed outside said discharge portion (13).

40. An assembly according to claim 29, in which said main portion (11) of the syringe body (10) is adapted to containing the lens (1) in the non-deformed state.

41. An assembly according to claim 23, in which, at its end in contact with the lens (1), said central strand (23) has a profile (25) defining a central or side space (26) for receiving said at least one upper haptic of said lens (1).

42. An assembly according to claim 41, in which said central strand (23) is connected to said side strands (21, 22) via a mechanical link mechanism (40) which automatically releases said central strand (23) from said side strands (21, 22) when said side strands reach said abutment (30).

43. An assembly according to claim 41, in which, at the end of discharge of the lens (1), said end profile (25) of the plunger (20), which profile defines said space (26), is disposed outside said discharge portion (13).

44. An assembly according to claim 41, in which said main portion (11) of the syringe body (10) is adapted to containing the lens (1) in the non-deformed state.

45. An assembly according to claim 23, in which, at the end of discharge of the lens (1), said end profile (25) of the plunger (20), which profile defines said space (26), is disposed outside the syringe body (10), in particular outside said discharge portion (13).

46. An assembly according to claim 23, in which said main portion (11) of the syringe body (10) is adapted to containing the lens (1) in the non-deformed state.

47. An assembly according to claim 1, in which, at the end of discharge of the lens (1), said end profile (25) of the plunger (20), which profile defines said space (26), is disposed outside said discharge portion (13).

48. An assembly according to claim 47, in which, at the end of discharge of the lens (1), said end profile (25) of the plunger (20), which profile defines said space (26), is disposed outside said discharge portion (13).

49. An assembly according to claim 47, in which said main portion (11) of the syringe body (10) is adapted to containing the lens (1) in the non-deformed state.

50. An assembly according to claim 1, in which said main portion (11) of the syringe body (10) is adapted to containing the lens (1) in the non-deformed state.

* * * * *